United States Patent
Pirzada et al.

(10) Patent No.: US 10,226,566 B2
(45) Date of Patent: Mar. 12, 2019

(54) SYSTEM AND PROCESS FOR REMOVING BODILY FLUIDS FROM A BODY OPENING

(71) Applicant: GENADYNE BIOTECHNOLOGIES, INC., Hicksville, NY (US)

(72) Inventors: Shahzad Pirzada, Old Westbury, NY (US); Chien Ming Goh, Syosset, NY (US)

(73) Assignee: GENADYNE BIOTECHNOLOGIES, INC., Hicksville, NY (US)

( * ) Notice: Subject to any disclaimer, the term of this patent is extended or adjusted under 35 U.S.C. 154(b) by 414 days.

(21) Appl. No.: 14/260,267

(22) Filed: Apr. 23, 2014

(65) Prior Publication Data

US 2015/0306303 A1    Oct. 29, 2015

(51) Int. Cl.
*A61M 1/36* (2006.01)
*A61M 1/00* (2006.01)

(52) U.S. Cl.
CPC ........ *A61M 1/3672* (2013.01); *A61M 1/0001* (2013.01); *A61M 1/0052* (2014.02); *A61M 1/0056* (2013.01); *A61M 1/0096* (2014.02)

(58) Field of Classification Search
CPC combination set(s) only.
See application file for complete search history.

(56) References Cited

U.S. PATENT DOCUMENTS 2,725,056 A * 11/1955 Tash ...................... A61M 5/155
                                                              604/122
4,898,572 A * 2/1990 Surugue ............... A61M 1/0001
                                                              604/6.09

(Continued)

FOREIGN PATENT DOCUMENTS

WO    2001085248 A1    11/2001
WO    2004060148 A2    7/2004
(Continued)

OTHER PUBLICATIONS

KCI Trackpad http://www.kci1.com/KCI1/accessories-tracpad; Earliest known publication Oct. 4, 2012.
(Continued)

*Primary Examiner* — Tatyana Zalukaeva
*Assistant Examiner* — Guy K Townsend
(74) *Attorney, Agent, or Firm* — Collard & Roe, P.C.

(57) ABSTRACT

There is a process and a system for removing body fluids from a body opening. The system can comprise a container having an inflow port and an outflow port. The inflow port is coupled to a fluid conduit, the outflow port is coupled to a pump. In one embodiment, disposed in the outflow port is a coagulant agent for coagulating bodily fluids. There can be one or more filters coupled to the container as well. In one embodiment at least one filter is coupled to the outflow port to prevent coagulated bodily fluids from leaving the container and flowing towards the pump. There can also be a process which involves providing at least one coagulant in the container, wherein the coagulant for coagulation of the body fluids and storing the coagulated body fluids in the container. There is also a process for assembling the container as well which in one embodiment includes providing both a coagulant and a filter coupled to the container. The container can also include support ridges or ribs suitable to support intake ports or outflow ports or surfaces of the container.

20 Claims, 17 Drawing Sheets

(56) References Cited

U.S. PATENT DOCUMENTS

| | | | |
|---|---|---|---|
| 4,988,342 A * | 1/1991 | Herweck | A61M 1/0013 604/321 |
| 5,234,403 A | 8/1993 | Yoda et al. | |
| 5,242,384 A * | 9/1993 | Robinson | A61M 1/3621 604/269 |
| 5,645,081 A | 7/1997 | Argenta et al. | |
| 6,220,453 B1 * | 4/2001 | Kitajima | B01D 19/0031 210/406 |
| 6,553,998 B2 | 4/2003 | Heaton et al. | |
| 6,936,037 B2 | 8/2005 | Bubb et al. | |
| 7,070,584 B2 | 7/2006 | Johnson et al. | |
| 7,216,651 B2 | 5/2007 | Argenta et al. | |
| 7,381,859 B2 | 6/2008 | Hunt et al. | |
| 7,722,582 B2 | 5/2010 | Lina et al. | |
| 7,732,655 B2 | 6/2010 | Cullen et al. | |
| 7,763,769 B2 | 7/2010 | Johnson et al. | |
| 7,772,454 B2 | 8/2010 | Addison et al. | |
| 7,951,100 B2 | 5/2011 | Hunt et al. | |
| 7,976,519 B2 | 7/2011 | Bubb et al. | |
| 8,058,499 B2 | 11/2011 | Silcock et al. | |
| 8,084,663 B2 | 12/2011 | Watson, Jr. | |
| 8,084,664 B2 | 12/2011 | Johnson et al. | |
| 8,097,272 B2 | 1/2012 | Addison | |
| 8,187,210 B2 | 5/2012 | Hunt et al. | |
| 8,246,592 B2 | 8/2012 | Lockwood et al. | |
| 8,350,116 B2 | 1/2013 | Lockwood et al. | |
| 8,409,156 B2 | 4/2013 | Kazala, Jr. et al. | |
| 8,444,611 B2 | 5/2013 | Wilkes et al. | |
| 8,460,257 B2 | 6/2013 | Locke et al. | |
| 2001/0055621 A1 * | 12/2001 | Baugh | A61L 24/0005 424/530 |
| 2002/0032112 A1 * | 3/2002 | Pages | B04B 5/0442 494/36 |
| 2002/0144939 A1 * | 10/2002 | Dolecek | A61M 1/3693 210/145 |
| 2002/0147094 A1 * | 10/2002 | Dolecek | A61M 1/3693 494/9 |
| 2002/0147098 A1 * | 10/2002 | Dolecek | A61M 1/3693 494/37 |
| 2002/0147099 A1 * | 10/2002 | Dolecek | A61M 1/3693 494/37 |
| 2002/0147101 A1 * | 10/2002 | Dolecek | A61M 1/3693 494/45 |
| 2002/0148787 A1 * | 10/2002 | Dolecek | A61M 1/3693 210/739 |
| 2002/0165575 A1 * | 11/2002 | Saleh | A61B 5/0215 606/200 |
| 2002/0182664 A1 * | 12/2002 | Dolecek | A61K 35/19 435/40.5 |
| 2003/0013590 A1 * | 1/2003 | Dolecek | A61M 1/3693 494/37 |
| 2003/0190368 A1 * | 10/2003 | Stoughton | A61K 38/57 424/556 |
| 2003/0222029 A1 * | 12/2003 | Muller | A61M 1/3693 210/739 |
| 2004/0011747 A1 * | 1/2004 | Dolecek | A61M 1/3693 210/787 |
| 2004/0082459 A1 * | 4/2004 | Min | A61M 1/3693 494/37 |
| 2004/0223857 A1 * | 11/2004 | Kline | A61M 1/3693 417/282 |
| 2009/0032111 A1 * | 2/2009 | Tong | A61B 5/14532 137/1 |
| 2009/0099498 A1 * | 4/2009 | Demers | A61M 1/106 604/6.09 |
| 2011/0224631 A1 | 9/2011 | Simmons et al. | |
| 2011/0315611 A1 * | 12/2011 | Fulkerson | A61M 1/3639 210/96.2 |
| 2012/0220963 A1 | 8/2012 | Hunt et al. | |
| 2012/0289881 A1 * | 11/2012 | Lyu | A61M 1/1678 604/9 |
| 2012/0309636 A1 * | 12/2012 | Gibbons | B01L 3/0275 506/9 |
| 2013/0292319 A1 * | 11/2013 | Fulkerson | A61M 1/1692 210/321.78 |
| 2013/0303960 A1 * | 11/2013 | Courtney | B82Y 15/00 604/5.02 |
| 2014/0187666 A1 * | 7/2014 | Aizenberg | A61L 33/0094 523/113 |
| 2014/0273064 A1 * | 9/2014 | Smith | G01N 33/57438 435/29 |
| 2015/0306303 A1 * | 10/2015 | Pirzada | A61M 1/0052 604/319 |
| 2015/0367062 A1 * | 12/2015 | Brugger | A61M 1/3646 210/646 |

FOREIGN PATENT DOCUMENTS

| | | |
|---|---|---|
| WO | 2005009488 A2 | 2/2005 |
| WO | 2009158129 A1 | 12/2009 |
| WO | 2009158131 A1 | 12/2009 |
| WO | 2010033574 A1 | 3/2010 |
| WO | 2010033613 A1 | 3/2010 |
| WO | 2010053870 A1 | 5/2010 |
| WO | 2010120776 A1 | 10/2010 |
| WO | 2010128281 A2 | 11/2010 |
| WO | 2010142959 A2 | 12/2010 |
| WO | 2011112724 A1 | 9/2011 |
| WO | 2011127188 A2 | 10/2011 |
| WO | 2012028842 A1 | 3/2012 |
| WO | 2012078556 A2 | 6/2012 |
| WO | 2012104584 A1 | 8/2012 |
| WO | 2012149242 A1 | 11/2012 |
| WO | 2012/172341 A2 | 12/2012 |
| WO | 2013019438 A1 | 2/2013 |
| WO | 2013022498 A1 | 2/2013 |
| WO | 2013071243 A2 | 5/2013 |
| WO | 2013071253 A1 | 5/2013 |
| WO | 2013074825 A1 | 5/2013 |
| WO | 2013116552 A1 | 8/2013 |

OTHER PUBLICATIONS

KCI Abdominal Dressing http://www.kci1.com/KCI1/vac-abdominal-dressing-system 2 pages; Earliest known publication Oct. 4, 2012.

International Search Report and Written Opinion of the International Searching Authority with Notice of Transmittal of the International Search Report and Written Opinion of PCT/US2015/026703.

International Preliminary Report on Patentability and Written Opinion of the International Searching Authority of PCT/US2015/026703.

* cited by examiner

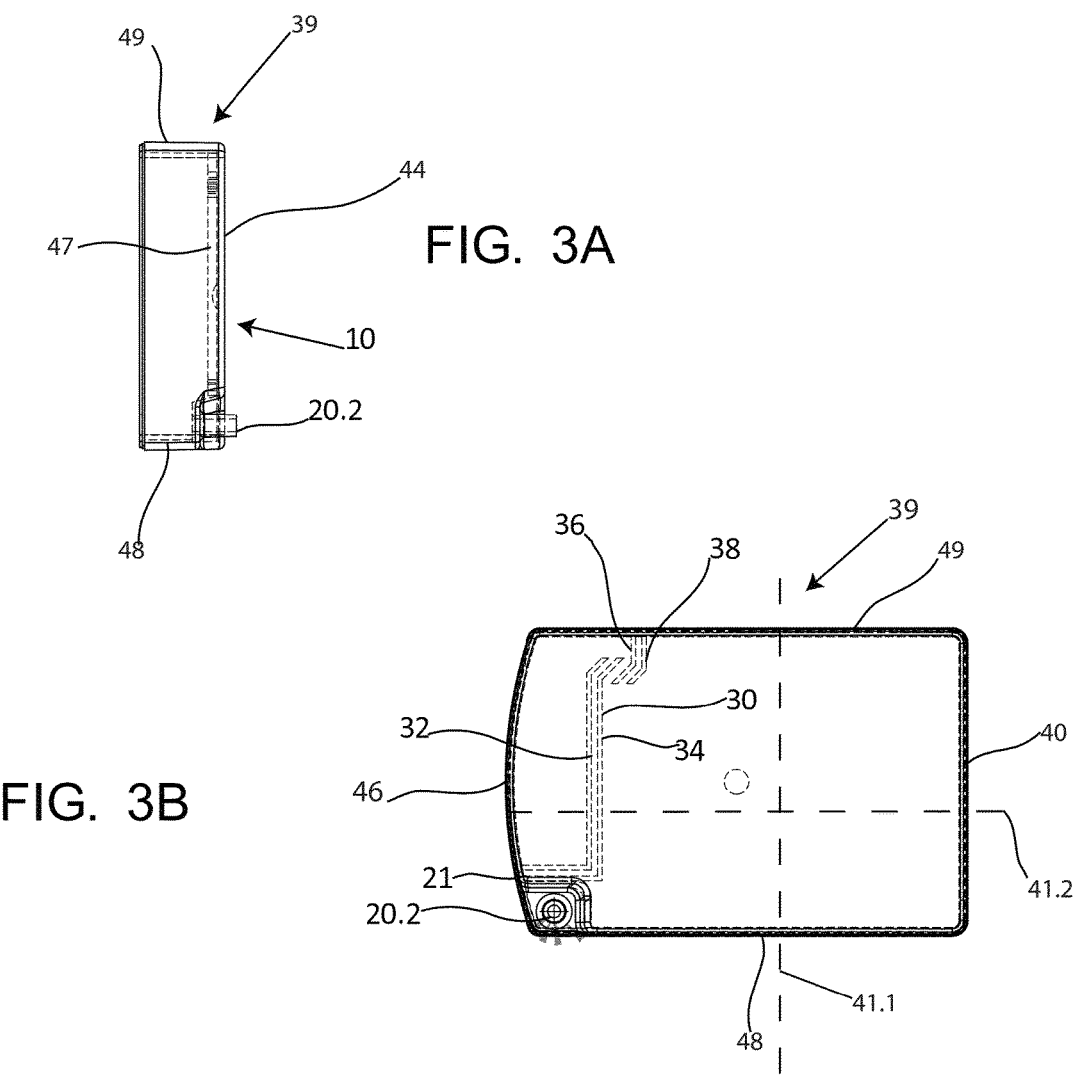

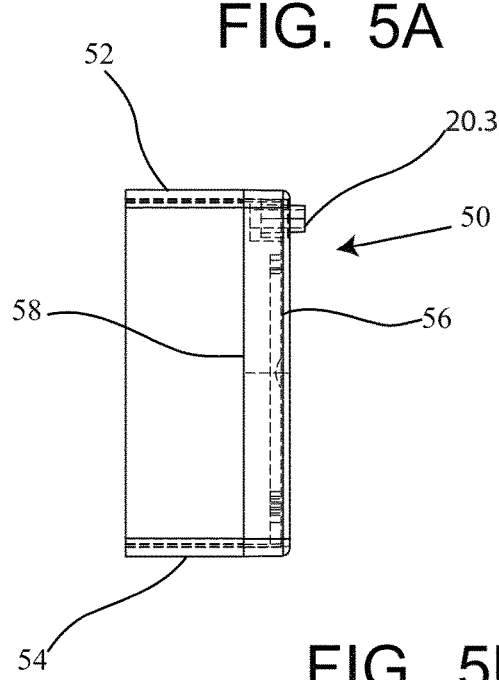
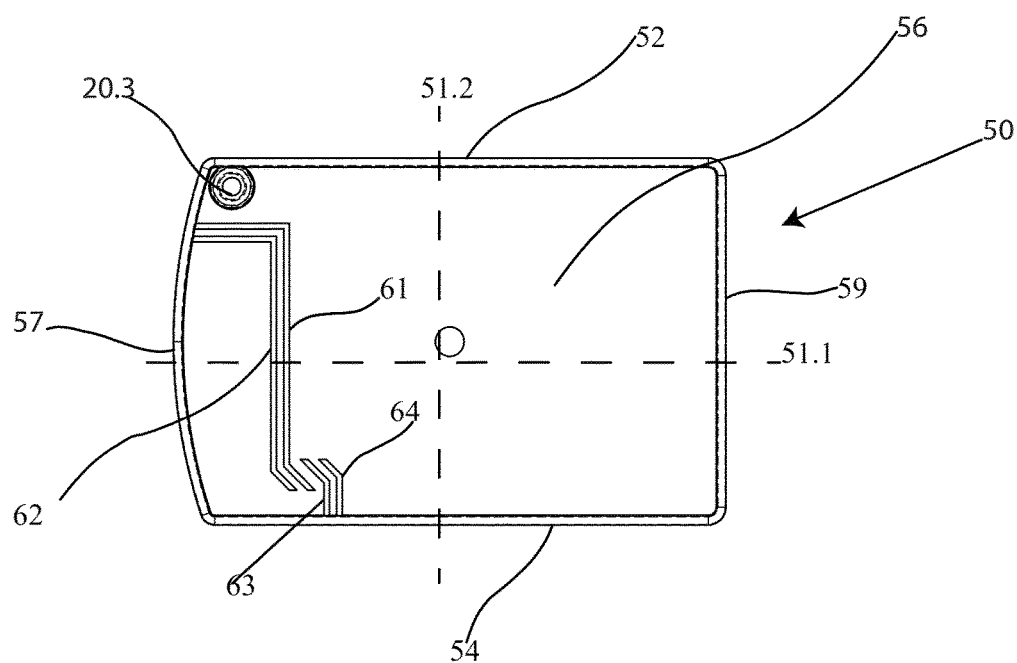

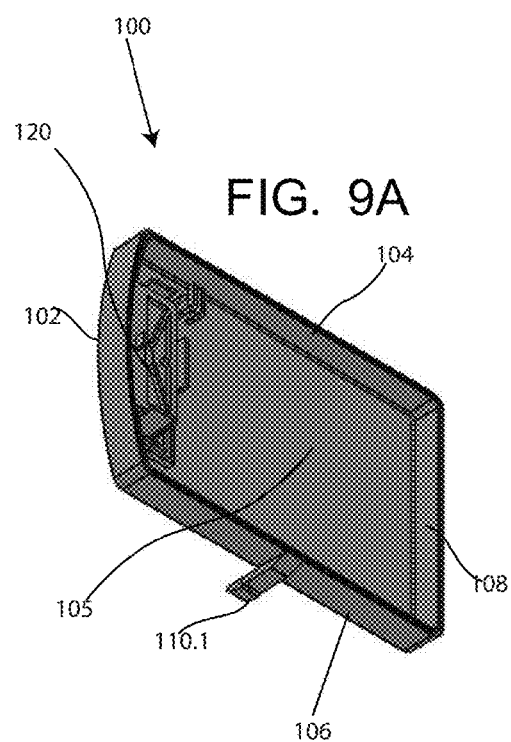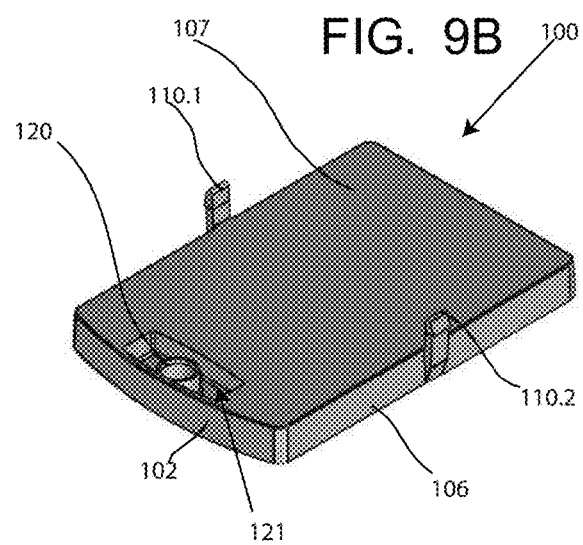

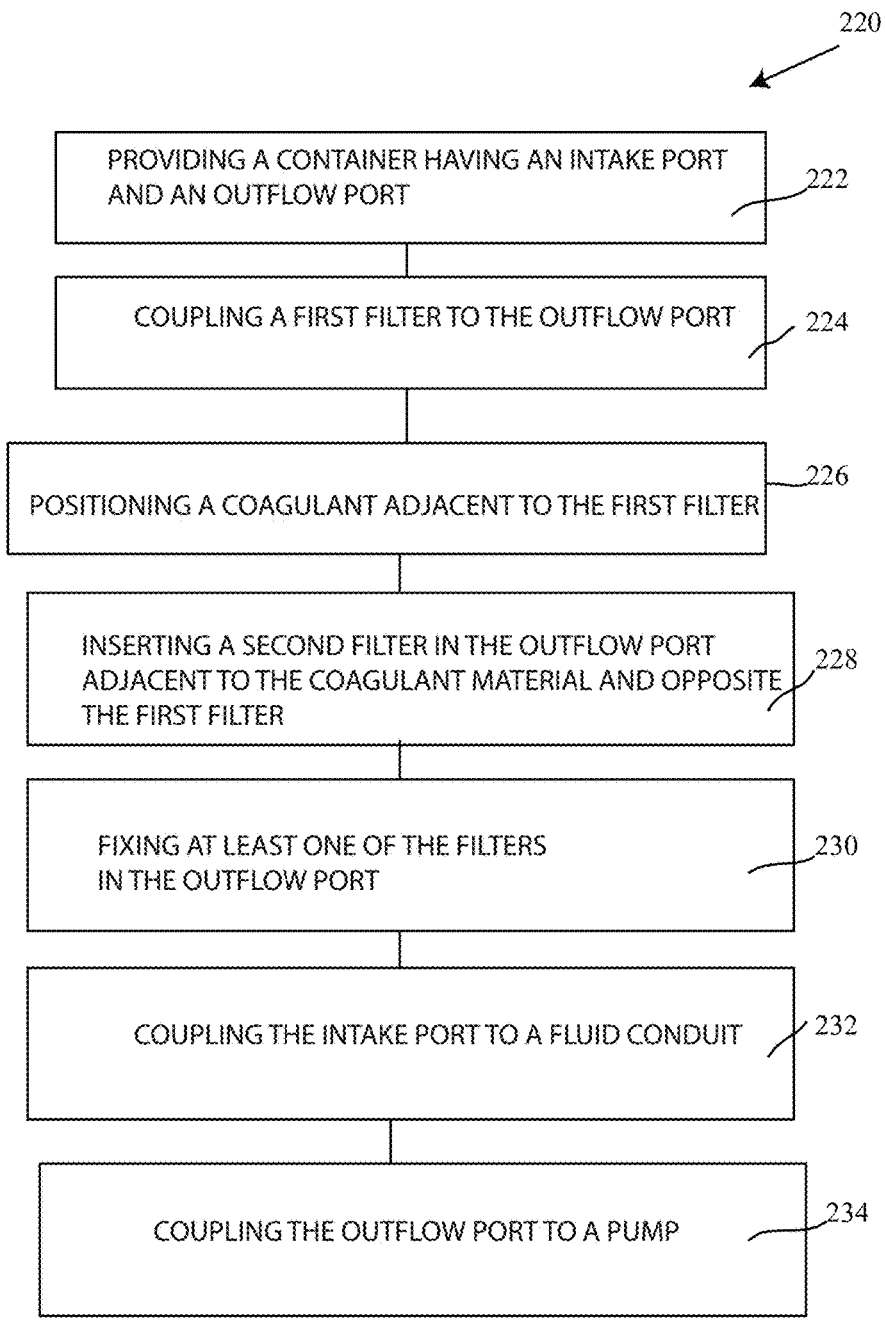

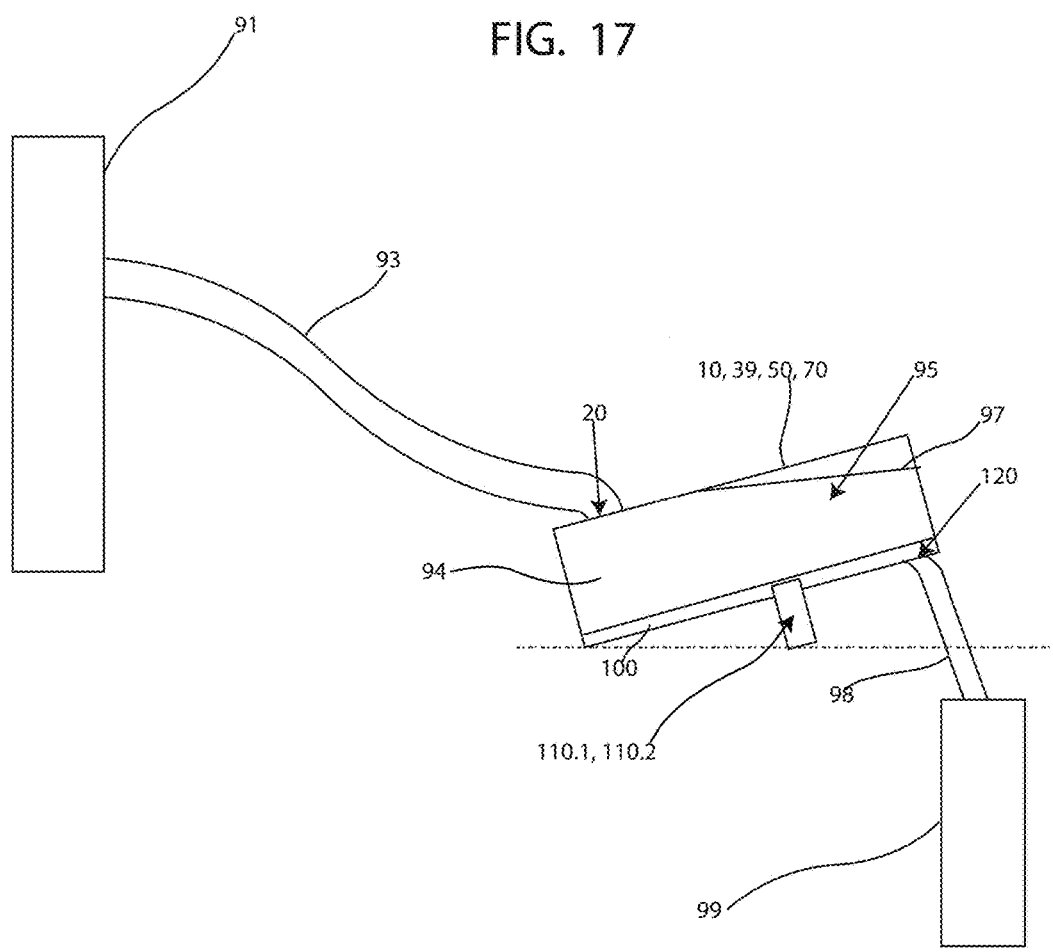

SYSTEM AND PROCESS FOR REMOVING BODILY FLUIDS FROM A BODY OPENING

BACKGROUND

One embodiment of the invention relates to a process and a system for removing body fluids from a body opening and then storing these bodily fluids in a container. While the process and system can work well, in some cases bodily fluids may end up compromising a pump system associated with the pumping of these bodily fluids. In contrast, in the past, such as with U.S. Pat. No 5,234,403 the disclosure of which is hereby incorporated herein by reference, blood collecting apparatus have used anticoagulant materials to keep blood flowing through the system and to prevent these fluids from solidifying in a container.

Therefore, one benefit of one embodiment of the invention is to at least partially trap bodily fluids inside of a container to then prevent the flow of these bodily fluids onto the pump.

SUMMARY

The invention relates to a process and a system for removing body fluids from a body opening. The system can comprise a container having an inflow port and an outflow port. The inflow port is coupled to a fluid conduit, the outflow port is coupled to a pump. In one embodiment, disposed in the outflow port is a coagulant agent for coagulating bodily fluids. There can be one or more filters coupled to the container as well. In one embodiment at least one filter is coupled to the outflow port to prevent coagulated bodily fluids from leaving the container and flowing toward the pump. There can also be a process which involves providing at least one coagulant in the container, wherein the coagulant is for coagulation of the body fluids and storing the coagulated body fluids in the container. There is also a process for assembling the container as well, which in one embodiment includes providing both a coagulant and a filter coupled to the container.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 3A is an outside end view along a latitudinal axis of a portion of another container of a larger size than FIG. 1A which does not include a base;

FIG. 3B is an outside view of the container of FIG. 3A;

FIG. 5A is a side view of a portion of a container which does not yet include a base and which is larger than the container of FIG. 3A;

FIG. 5B is an inside view of the portion of the container of FIG. 5A;

FIG. 9A is a solid perspective inside view of a base section of the container which can be coupled to any one of the portions of a container shown in FIGS. 1A-8B;

FIG. 9B is a solid perspective outside view of the base of the container shown in FIG. 9A;

FIG. 16 is a flow chart showing an example of multiple different processes for assembling a container for holding bodily fluids; and FIG. 17 is a schematic drawing of a configuration of the assembled container in combination with a dressing and a pump.

DETAILED DESCRIPTION

Figure 1A:
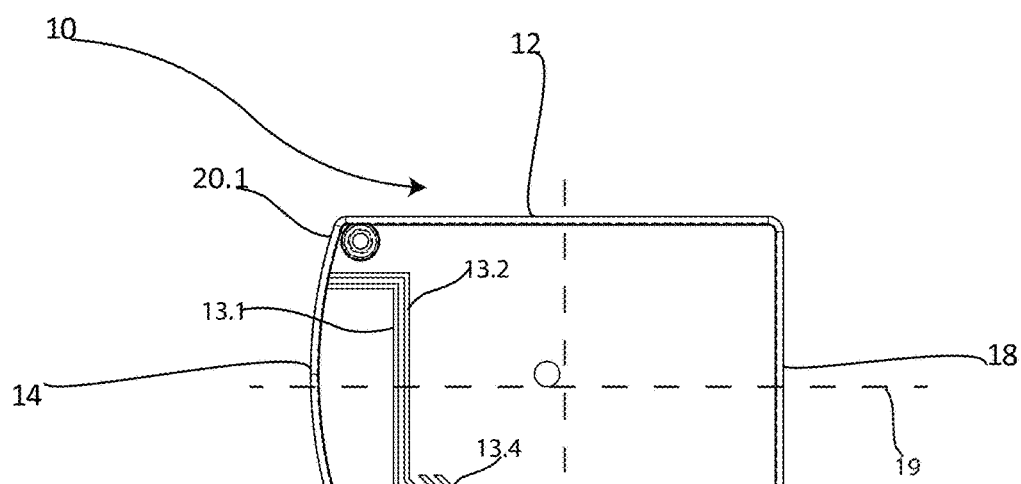
FIG. 1A is an inside view of a portion of a first sized container which does not include a base.
Figure 1B:
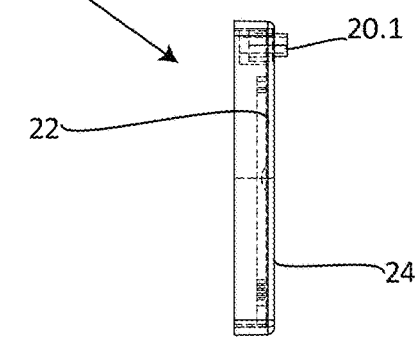
FIG. 1B is an end view of the container of FIG. 1A taken along side 18.
Figure 10A:
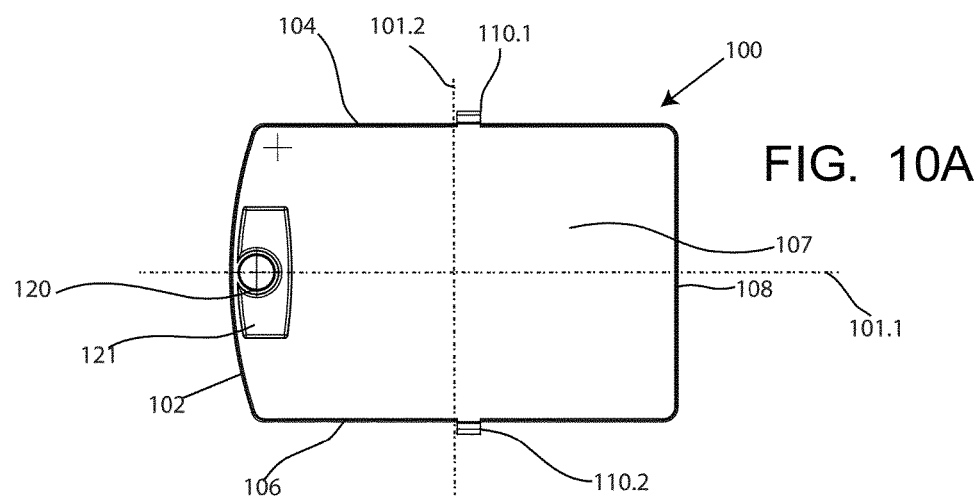
FIG. 10A is an outside view of the base of the container shown in FIG. 9A.
Figure 10B:
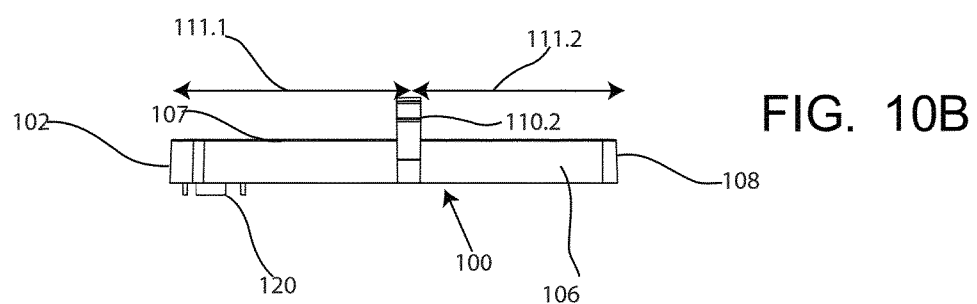
FIG. 10B is a side view of the base of the container shown in FIG. 9A and 10A.
Figure 10C:
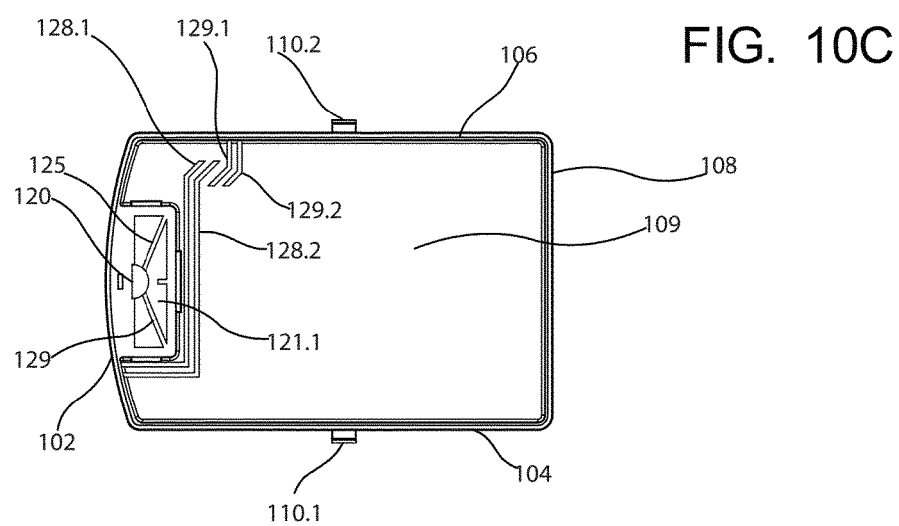
FIG. 10C is an inside view of the base of the container shown in FIG. 9A and in FIG. 10A.

FIG. 1A is an inside view of a portion of a first sized container which does not include a base, wherein the complementary base is shown in FIGS. 10A-10C. In this view there is shown a container portion 10 having sides 12, 14, 16, and 18, as well as an intake or inflow port 20.1. Portion 10 can be of any suitable size but in at least one embodiment, it can be combined with base 100 to form a 200 cc or substantially 200 cc container. There is also an inside face 22 and an outside face 24 (See FIG. 1B which is taken along side 18). Sides 14 and 18 extend along latitudinal axis 17 while sides 12 and 16 extend along longitudinal axis 19. Side 14 can be curved. The container can also be made from any suitable material and be made from any suitable shape. In at least one embodiment container 14 is made from plastic. The inside face 22 and outside face 24 as well as port 20.1 are supported by ribs or support ridges 13.1, 13.2, 13.3 and 13.4.

Figure 2A:
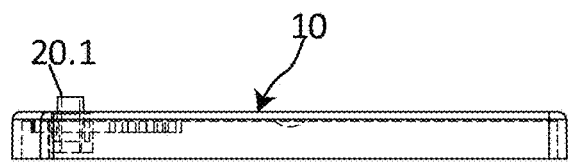
FIG. 2A is a side view of the container of FIG. 1A taken along side 16.
Figure 2B:
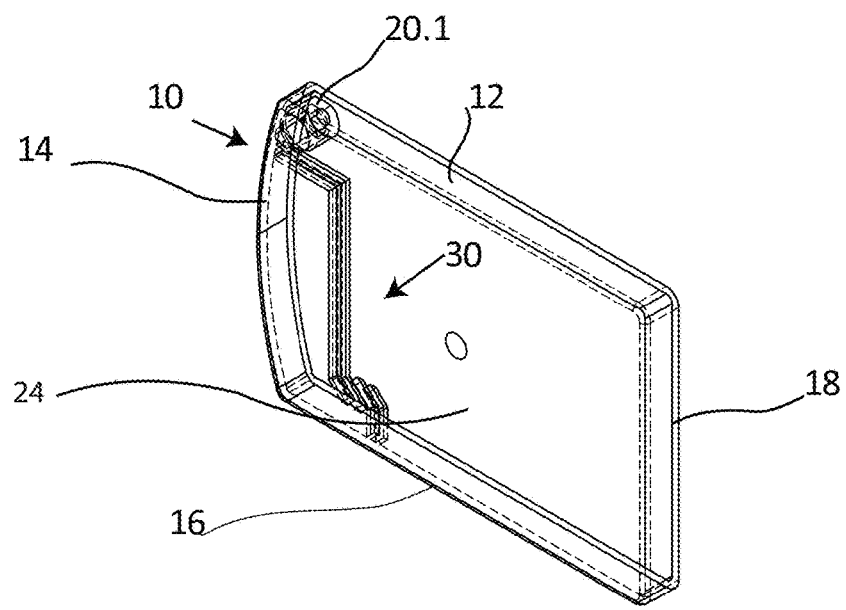
FIG. 2B is an outside view of the container of FIG. 1A.

The inflow or intake port is configured to be coupled to a fluid conduit such as a hose which receives fluid from a bodily opening such as an opening from an operation or a wound. FIGS. 2A and 2B show different views such that FIG. 2A is a side view of the container of FIG. 1A taken along side 16, and FIG. 2B is an outside view of the container of FIG. 1A. FIG. 3A is an outside end view along latitudinal axis 41.1 of a portion of another container 39 of a larger size than FIG. 1A which does not include a base such as the base shown in FIG. 10A-10C. This container can be larger such that it is any suitable size and can be configured to receive approximately 400 cc of bodily fluid. It includes sides 48 and 49 which extend along longitudinal axis 41.2 and sides 40 and 46 which extend along latitudinal axis 41.1 (See FIG. 3B). There is also an exterior side 44 and an interior side 46. An intake or inflow port 20.2 is positioned on the portion of the container to receive fluid as disclosed in FIG. 1A. There are also interior extensions or ribs 30 which are configured to provide interior support for surface 44.

Figure 4A:
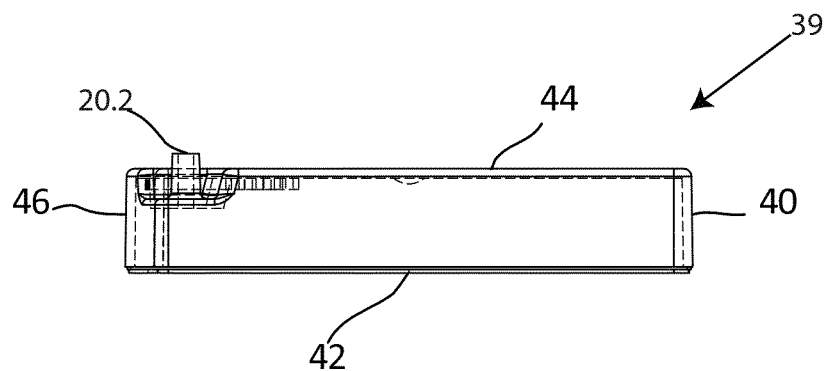
FIG. 4A is a side view of the container of FIG. 3A.
Figure 4B:
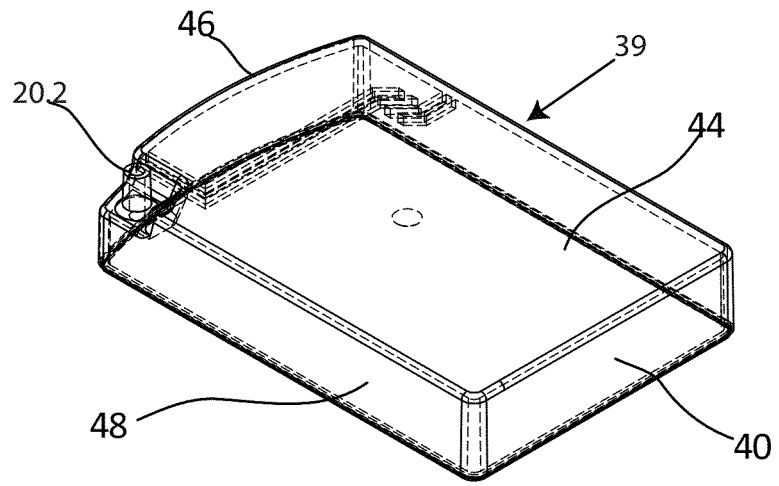
FIG. 4B is a perspective view of the container of FIG. 3A.

FIG. 3B is an outside view of the container 39 of FIG. 3A. This view shows ribs 32, 34, 36 and 38. FIG. 4A is a side view of the container of FIG. 3A while FIG. 4B is a perspective view of the container of FIG. 3A. FIG. 4A shows a side view of container 39. This view shows front face 44, and sides 40 and 46. A longitudinal side 42 is also shown. Intake port 20.2 is shown extending above front face 44 and is shaped substantially cylindrically, (See FIG. 4B). There is a recessed region surrounding this intake port 20. Intake port 20.2 is configured to be coupled to a fluid conduit for importing fluid from an opening in a body. FIG. 4B is a perspective view of the container shown in FIG. 4A. This view shows longitudinal side 48 as well as ends 40 and 46.

FIG. 5A is a side view of a portion of a container 50 which does not yet include a base and which is larger than the container of FIG. 3A. This portion of a container 50 can be in at least one embodiment size for 600 cc of fluid in a container when combined with a base. With this design, there is shown a front outer surface 56 as well as an inside surface 58. Sides 52 and 54 form longitudinal sides of container portion 50. Intake port 20.3 is shown as substantially cylindrical and recessed into the housing. FIG. 5B is an inside view of the portion of the container of FIG. 5A. This view shows latitudinal line 51.2 and longitudinal line 51.1. Sides 52 and 54 are substantially longitudinally extending sides while sides 57 and 59 are substantially latitudinally extending sides. As shown there are ribs 61, 62, 63, and 64 extending on an inside face 58 of this container portion 50. These ribs are configured to provide support for the intake port and the outflow port.

Figure 6A:
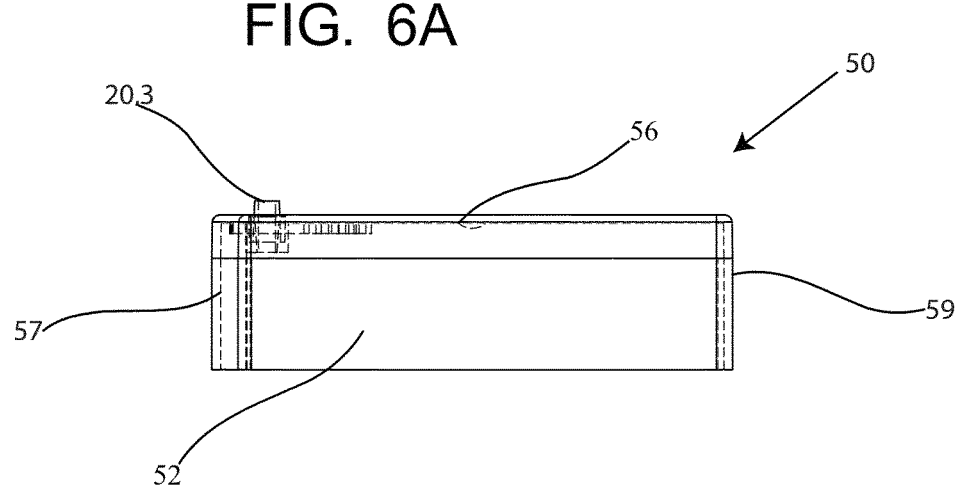
FIG. 6A is a side view of the portion of the container of FIG. 5A.
Figure 6B:
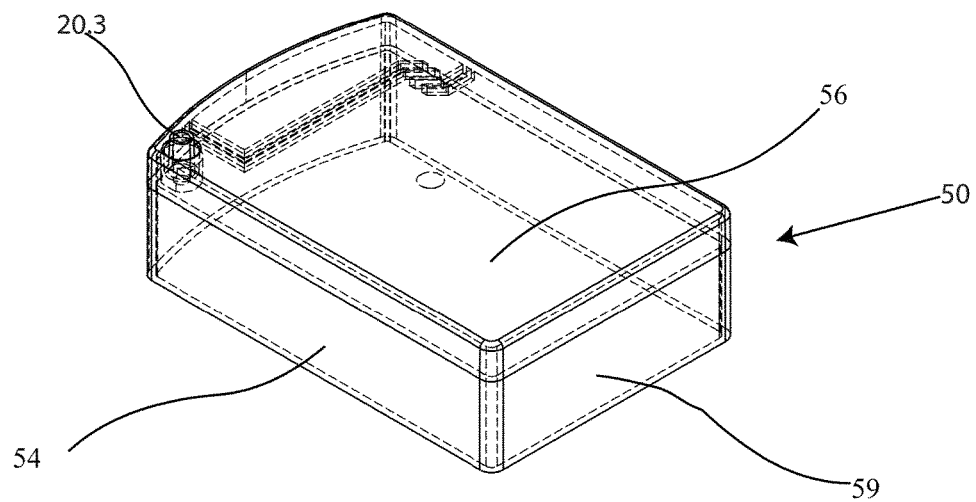
FIG. 6B is a perspective view of the portion of the container of FIG. 5A.

FIG. 6A is a side view of the portion of the container portion 50 of FIG. 5A. This view shows longitudinal side 52, end sides 57 and 59 as well as a front surface 56. Intake port 20.3 is shown extending above front surface 56. FIG. 6B is a perspective view of the portion of the container 50 of FIG. 5A wherein this view shows intake port 20.3 as well as sides 54 and 59 and front face 56.

Figure 7A:
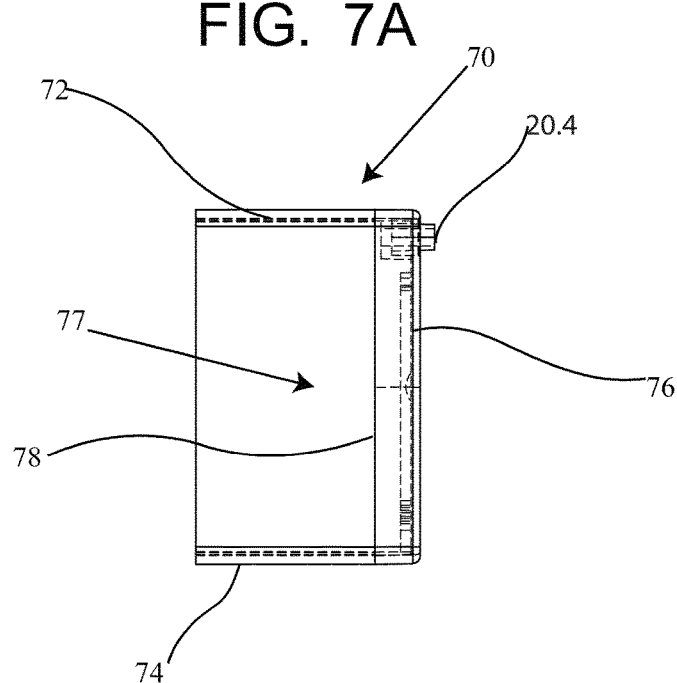
FIG. 7A is a side view of another portion of a container that is larger than that shown in FIG. 5A.
Figure 7B:
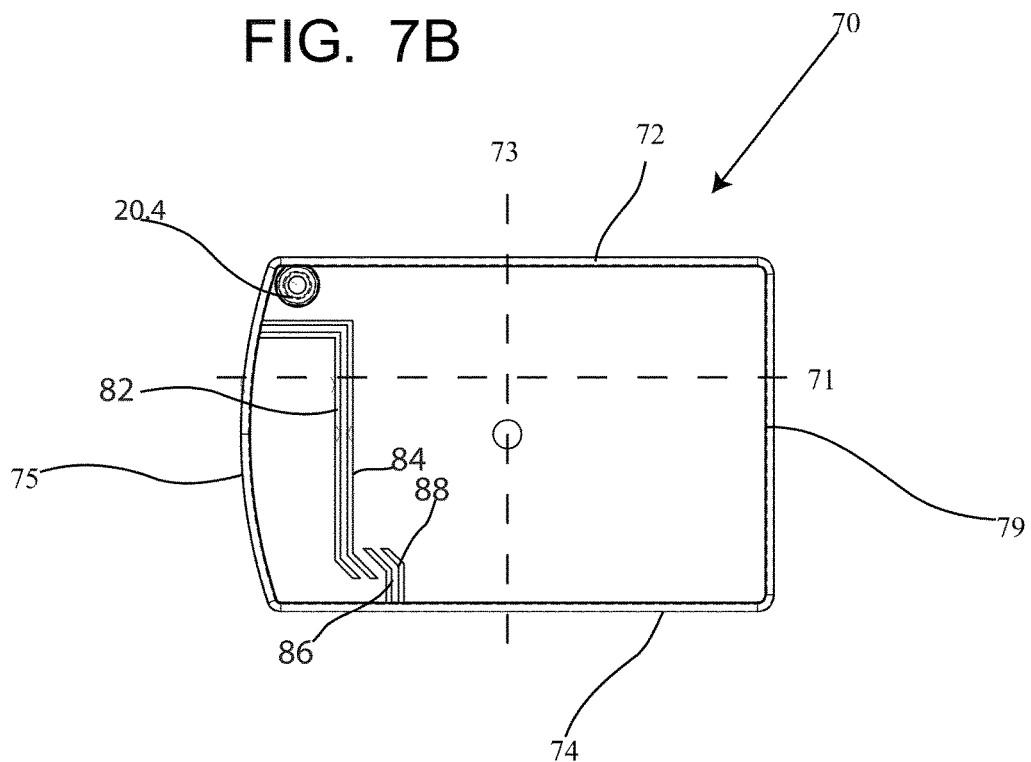
FIG. 7B is an inside view of the portion of the container.

FIG. 7A is a side view of another portion of a container 70 that is larger than that shown in FIG. 5A. For example, in at least one embodiment, the size of the container when formed from portion 70 can be 800 cc. This view shows sides 72 and 74 which are longitudinal sides as well as front surface 76. Intake port 20.4 is shown both recessed into surface 76 and extending above surface 76. There is also shown an inside area 77 which is bounded by sides 72 and 74 and also an inside surface 78. FIG. 7B is an inside view of the portion of the container 70. This view shows inside surface 78 which also shows ribs or supports 82, 84, 86 and 88 as well as the inside view of intake port 20.4. Sides 72 and 74 extend along or at least parallel to longitudinal axis 71. Sides 75 and 79 extend in a direction substantially parallel to latitudinal axis 73. As shown side 75 can be formed in a curved shape. Ribs, 82, 84, 86, 88 are configured to support surface 76 as well as port 20.4 These ribs or supports can be shaped in any suitable manner wherein at least one rib is substantially L-shaped.

Figure 8A:
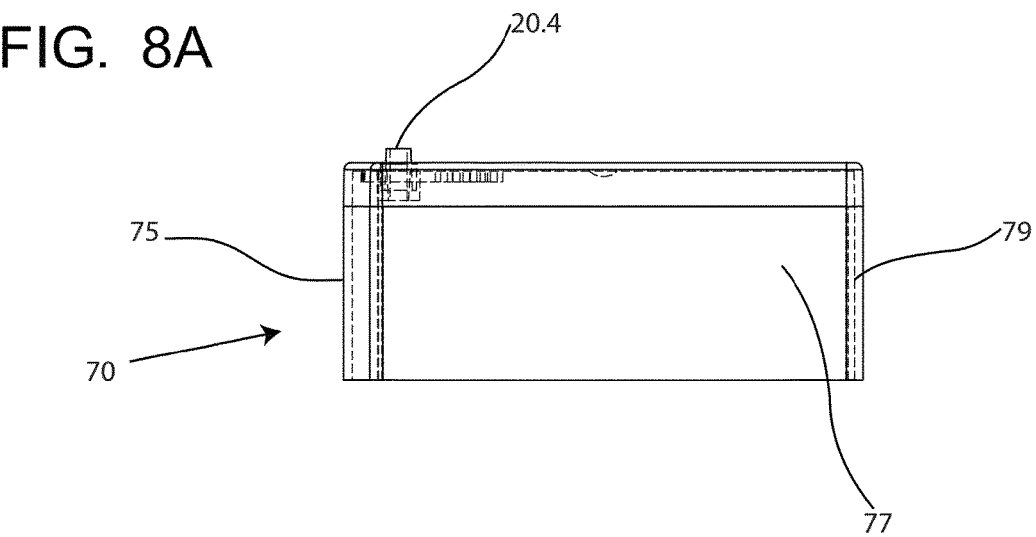
FIG. 8A is a side view of the portion of the container as shown in FIG. 7A.
Figure 8B:
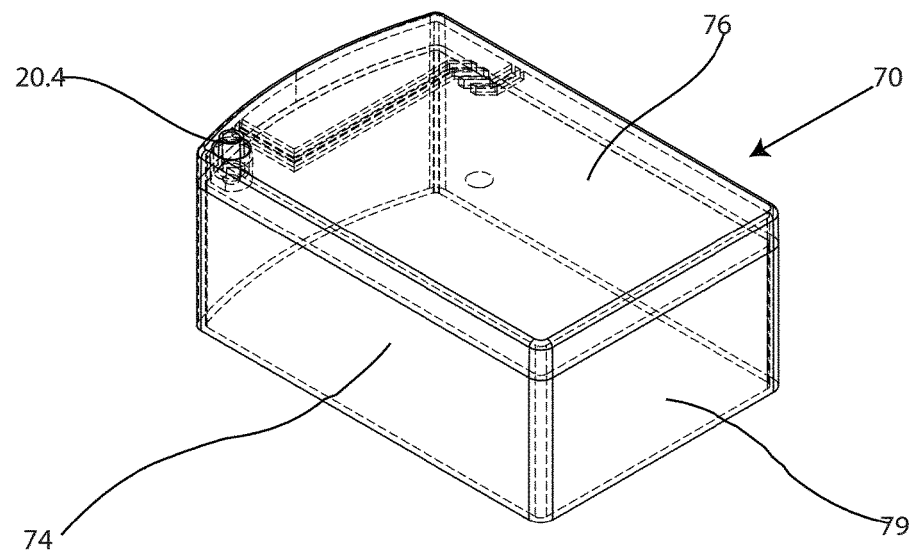
FIG. 8B is a perspective view of the portion of the container shown in FIG. 7A.

FIG. 8A is a side view of the portion of the container 70 as shown in FIG. 7A. In this view intake port 20.4 is shown extending substantially above surface 76. In addition sides 75 and 79 are also shown. FIG. 8B is a perspective view of the portion of the container shown in FIG. 7A. Sides 74 and 79 are shown along with front surface 76. Intake port 20.4 is shown recessed into front surface 76 and extending above front surface 76.

Each of these sections or portions of a container such as portion 10, 39, 50 and 70 can be coupled to an opposing base section 100 shown in FIGS. 9A-10C to form a fluid tight container for housing bodily fluids such as blood. A fluid conduit for feeding fluid into the container can be coupled to any one of intake ports 20.1, 20.2, 20.3, 20.4. In addition, a pump air fluid port can be coupled to outflow port 120 shown in FIG. 10A. This allows for air to be drawn from the container creating negative pressure inside of the container to draw fluid inside of the container formed by base 100 coupled with any one of portions 10, 39, 50 or 70.

FIG. 9A is a solid perspective inside view of a base section 100 of the container which can be coupled to any one of the portions of a container shown in FIGS. 1A-8B. This view shows an inside surface 105 along with latitudinally extending sides 102 and 108. Longitudinally extending sides 104 and 106 extend opposite each other such that sides 102, 104, 106, 108 form sides to the base which are coupled to the corresponding portion of the container 10, 39, 50 or 70. Support elements 110.1 and 110.2 (See FIG. 9B) extend from outside surface 107. These support elements 110.1 and 110.2 allow for the device to be positioned to keep fluid from flowing into outflow port 120.

FIG. 10A is an outside view of the base 100 of the container shown in FIG. 9A. In this view there is shown outer surface 107, along with sides 102, 104, 106, and 108. Outflow port 120 is shown recessed into outer surface 107 via recessed region 121. Recessed region 121 functions as a recessed portion which forms a surface indented from outer surface 107. Supports 110.1 and 110.2 are shown extending out from surface 107 to provide a support for tilting the container one side. These supports extend along perpendicular or substantially perpendicular to surface 107. Sides 104 and 106 extend substantially parallel to longitudinal axis 101.1 while sides 102 and 108 extend along substantially parallel to latitudinal axis 101.2. Supports 110.1 and 110.2 can be positioned substantially offset from a center position on base 100 so as to support a lean of the device from one side to the other. For example as shown in FIG. 10B there are extension lines 111.1 and 111.2. Extension line 111.1 extends from an end 102 to a center point of support 110.1 or 110.2. Extension line 111.1 can be longer than extension line 111.2 which extends from end 108 to a center point of support 110.1 or 110.2. This creates a biased offset lean for the compartment so that it leans to one side and biases the blood collection on one side. if extension line 111.1 is longer, than the majority of the weight or mass collected inside of the container would be on the side of end 102 so that the container would lean to one side. In at least one alternative embodiment, the extension lines 111.1 and 111.2 are even in length so that the supports are positioned in the center region of the base. Alternatively, in another embodiment extension line 111.2 can be longer than extension line 111.1 so that the lean is in the opposite direction. FIG. 10C is an inside view of the base of the container shown in FIG. 9A and in FIG. 10A, This view shows inside surface 109 as well as sides 102. Outflow port 120 along with support ridges or ribs 125 and 129 are shown on this inside face. Support ridges or ribs 125 and 129 support port 120 as well as surface 121.1 of recessed region 121. In addition, support ridges or ribs 128.1 and 128.2 are used for support of surface 107 while support ridges or ribs 129.1 and 129.2 are also used for support. Ribs 128.1 and 128.2 are substantially L-shaped while ribs 129.1 and 129.2 are substantially V-shaped. Ribs or supports or support ridges 125 and 129 can be formed in any suitable shape and can be formed as a substantially V-shaped brace for port 120.

Figure 11A:
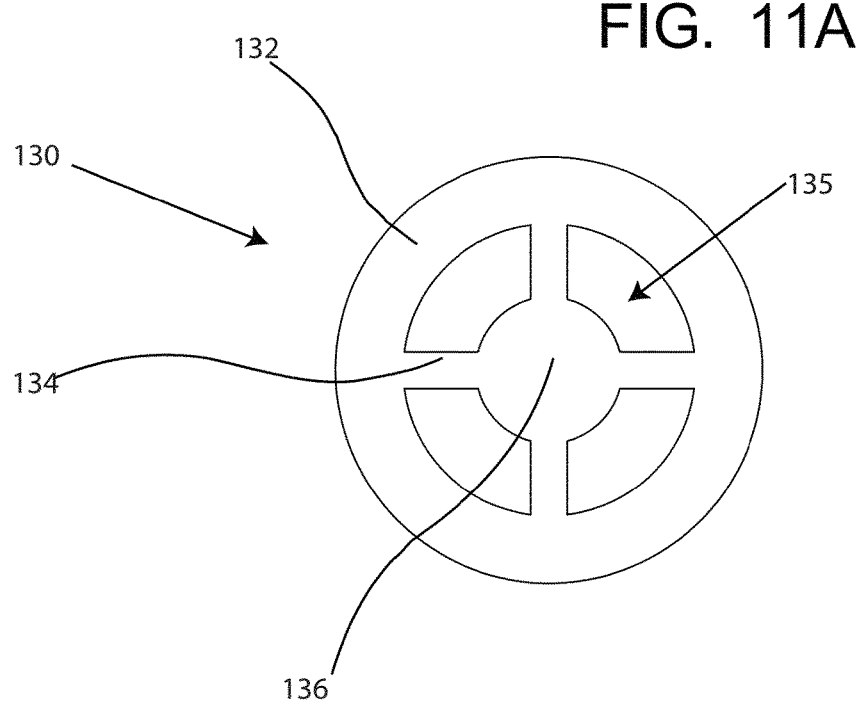
FIG. 11A is a plan view of a retainer button for holding a filter.
Figure 11B:
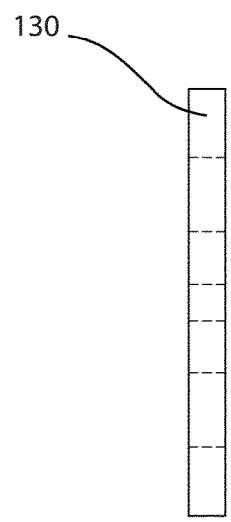
FIG. 11B is a side view of the retainer button shown in FIG. 11A.
Figure 12A:
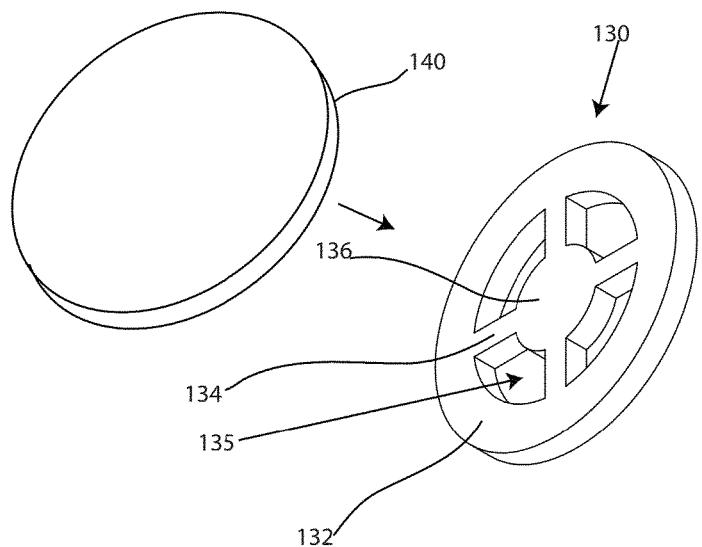
FIG. 12A is a side-exploded view of the filter and retainer button in unassembled form.
Figure 12B:
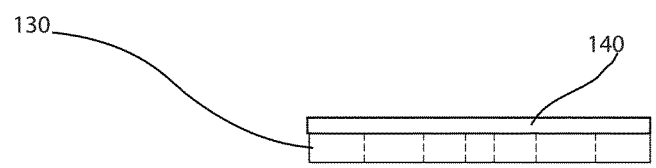
FIG. 12B is a side view of the filter and retainer button in assembled form.
Figure 13:
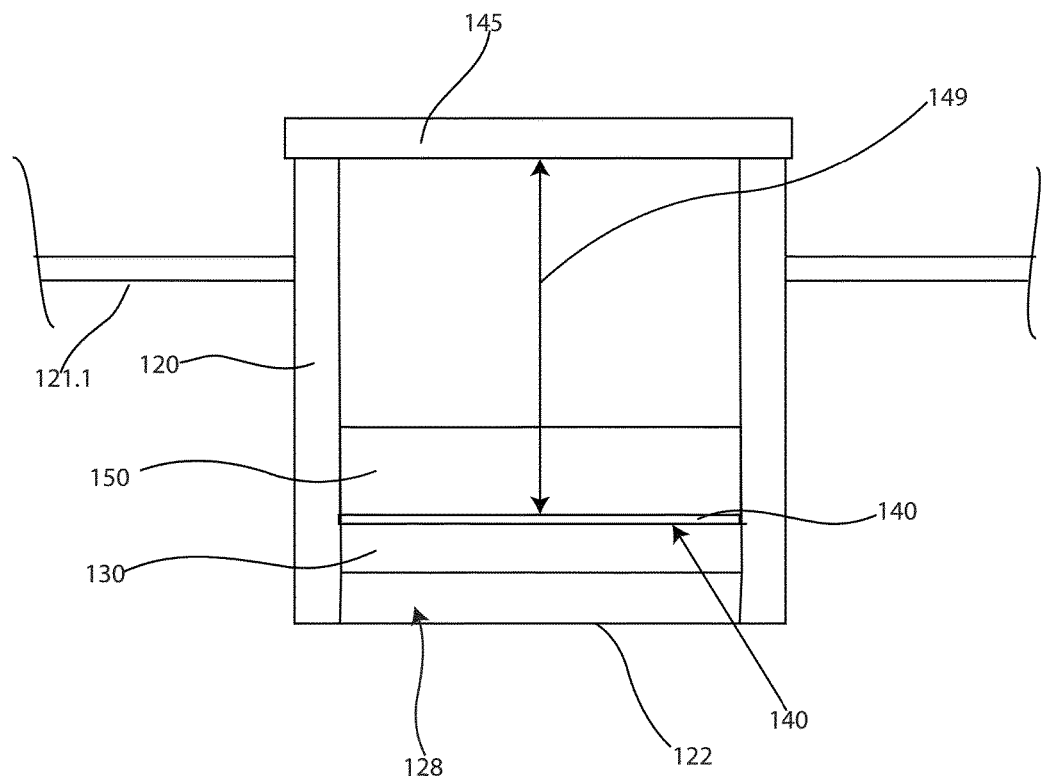
FIG. 13 is a side view of the first configuration of filter(s) and a coagulant in an outflow chamber of the container.

Outflow port 120 is configured to be coupled to a fluid conduit on to a pump such as a vacuum or air pump. To keep blood from flowing into mechanics of a pump (See FIG. 17) at least one filter is placed in the outflow port 120. While one filter can be placed at the inside region of the outflow port, another filter can be placed along the channel of the outflow port 120. This other filter can be supported by a frame 130 which can be structured as a cross-shaped button which has gaps or holes 135 which allow air or fluid to pass therethrough. Frame 130 can form a solid backing structure to a filter such as filter 140. FIG. 11A is a plan view of this support frame 130 which shows an outer rim 132, arms 134, a central support 136 and gaps or openings 135. A side view of this support frame is shown in FIG. 11B. FIG. 12A shows an exploded-perspective view of the filter material 140 and support 130. This filter material 140 can be coupled to support 130 in any suitable known manner such as through an adhesive or by simply placing it on the inside of the outflowing port whereby the negative pressure from the pump keeps this filter 140 on the support frame 130. FIG. 12B is a side view of the filter 140 and the support frame or retainer button 130 in assembled form. FIG. 13 is a side view of the first configuration of filter(s) 140 and 145 and coagulant 150 in an outflow port 120. Coagulant 150 can also be referred to as a solidifier or solidifier agent. It can be in powder form or any other suitable form.

Filters 145 and 140 form a region 149 shown by the arrow extending between filters 140 and 145 for the placement of the coagulant material. Filters 140 and 145 can be made from any suitable material and in at least one embodiment are made from a PTFE material to form PTFE filters. In at least one embodiment this PTFE can be Polytetrafluoroethylene. At least one filter such as filter 140 can be removable, whereby one can grasp arms 134 or any part of frame 130 or filter 140 and remove the filter from the container.

Figure 14:
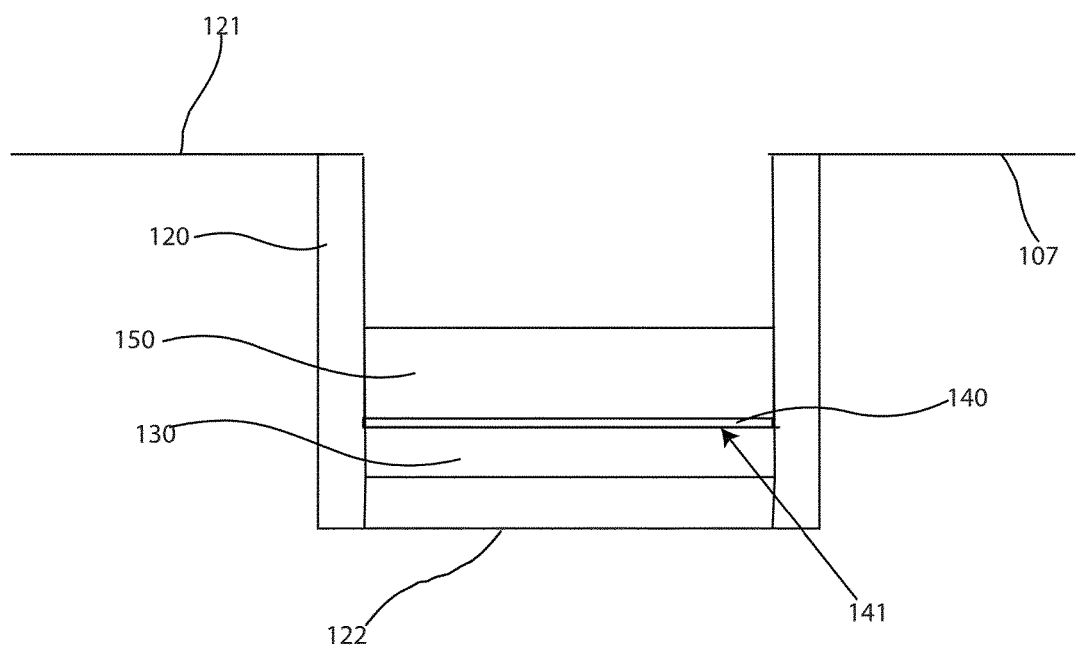
FIG. 14 is a side view of a second configuration of the filter and coagulant in an outflow chamber of the container.

Alternatively, filter 145 can also be selectively added or removed from the container or permanently or semi-permanently coupled to the container. In at least one embodiment, filter 140 and frame 130 can be removable or alternatively in another embodiment be permanently or semi-permanently coupled to the container and/or port 120. Filter 140 is shown sitting on or coupled to support frame 130 which is shown friction fit and pressed inside of port 120. Port 120 includes walls 128 and an outflow end 122 which flows out and into a fluid conduit such as that shown in FIG. 17. Side walls 121.1 of recessed region 120 are shown as a cross-sectional view which shows that port 120 extends both inside of the chamber as well as outside of the chamber but within the recessed region 121. FIG. 14 is a side view of a second configuration of the filter and coagulant 150 in an outflow port 120 of the container (95 See FIG. 17).

Figure 15:
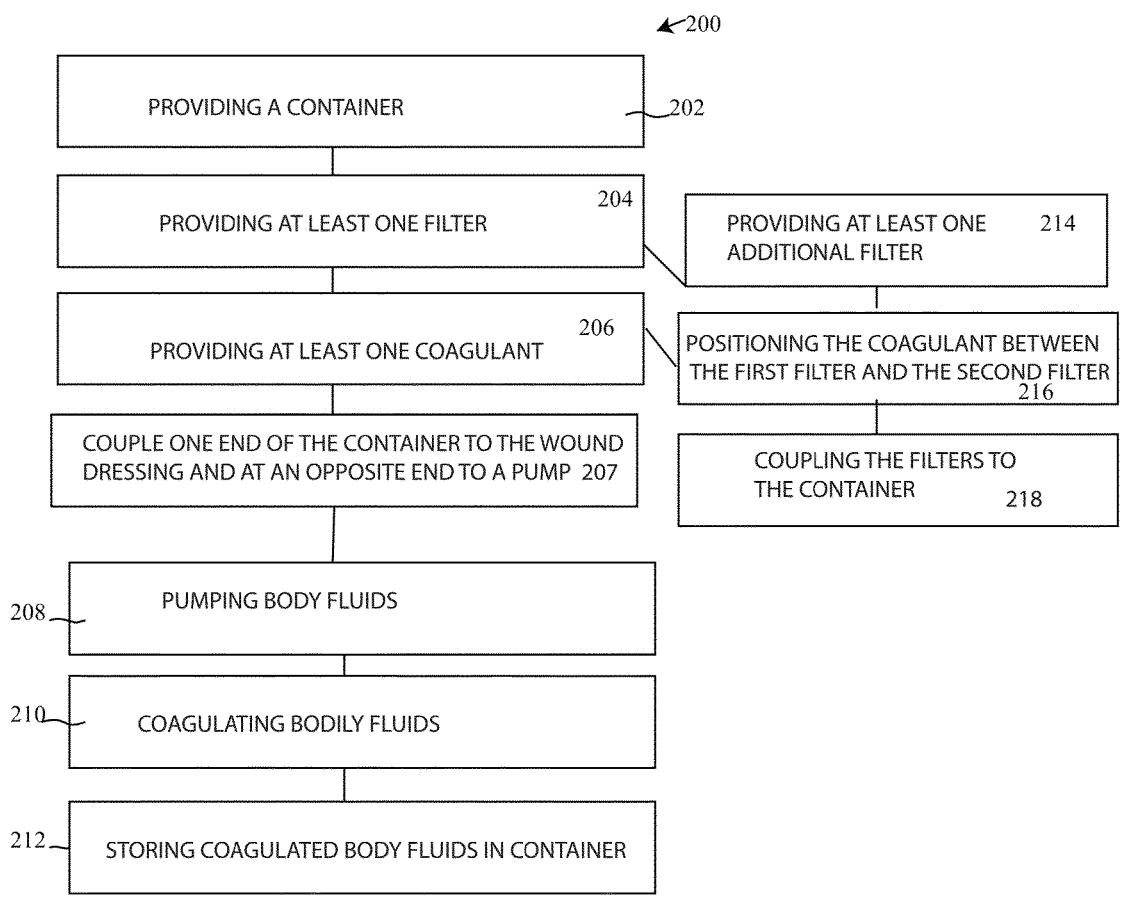
FIG. 15 is a flow chart showing an example of multiple different processes for removing bodily fluids.

FIG. 15 is a flow chart showing an example of multiple different processes for removing bodily fluids from an opening in a human body. For example, the flow chart 200 can include a first series of steps 202 to 212 for the process for filtering the blood as associated with the design of FIG. 14. For example, the process starts in step 202 where the user provides a container. A container such as container 95 can be comprised of a container portion such as any one of container portions 10, 39, 50, 70 coupled to base 100. Next, in step 204 the user can provide at least one filter. In at least one embodiment, the filter can be positioned in the outflow port such as outflow port 120 of the container. Next, in step 206 the user can provide at least one coagulant, wherein this coagulant can be positioned upstream of the at least one filter such as filter 140 or positioned adjacent to filter 145. In all likelihood, if only one filter is used, the filter would be placed downstream of the coagulant solution to trap the coagulant solution on a side toward the container so as to influence the fluid such as blood in the container to gel or coagulate and not pass through filter 140 and into a pump's mechanisms. The user can couple the container at one end to the wound dressing. The user can also couple the container at an opposite end to a pump in step 207. Next, once the container is coupled to a wound or opening to a body such as a dressing and at an opposite end to a pump mechanism, the pump can pump bodily fluids in step 208. The initiation of the pump 208 creates a negative pressure inside of the container to draw blood or other bodily fluids into the container. Once the blood of body fluids come in contact with the coagulant, the blood will coagulate, solidify or form a gel in step 210 which will prevent it from leaving the container and then harming a downstream pump. Thus, in step 212 the body fluids are stored inside of the container. In this process the steps can be performed in any suitable order. In addition, these above mentioned steps are optional relative to the purpose of the task to be performed. Additional steps can also be provided such as providing at least one additional filter such as filter 145, and then in step 216 positioning the coagulant between the first filter and the second filter. Next, the filters can be coupled to the container in step 218.

FIG. 16 is a flow chart showing an example of multiple different processes for assembling a container for holding bodily fluids. For example, the process or flow chart 220 can start in step 222 wherein there is the step of providing a container having an intake port and an outflow port. Next, in step 224, a first filter can be coupled to the outflow port. This filter can be either filter 140 or filter 145. Next, in step 226, the coagulant can be positioned adjacent to the first filter. Next, in step 228 the second filter can be inserted in the outflow port, adjacent to the coagulant and on an opposite side of the first filter. Next, in step 230, at least one of the filters is fixed in the outflow port. Next, in step 232 an intake port such as port 20 can be coupled to a fluid conduit such as fluid conduit 93 (FIG. 17). Next, in step 234 the outflow port is coupled to a pump such as pump 99 (See FIG. 17). Coupling pump 99 to an output port such as port 120 can be a fluid conduit 98. The steps listed above in FIGS. 15 and 16 can be performed in any suitable order.

FIG. 17 shows a schematic diagram of the container 95 comprising a container portion such any one of portion 10, 39, 50 or 70 coupled to a base 100. With this design, there is a fluid conduit 93 which is coupled at one end to a body dressing 91. At an opposite end fluid conduit 93 is coupled an to intake port such as any one of intake ports 20.1, 20.2, 20.3, 20.4 of container 95. Container 95 can be set to balance on supports 110.1 and 110.2 (See FIGS. 10A-10C). Container 95 has an outflow port 120 which is coupled to a fluid conduit 98 which allows fluid such as air to flow into a pump 99. Fluid conduits 93 and 98 can be made from any suitable material such as a hose material and be coupled to the ports 20.1, 20.2, 20.3, 20.4 and 120 so that a fluid tight or substantially fluid tight seal is formed. When pump 99 is started, it draws air or any other suitable gaseous form through the pump to create a negative pressure inside of container 95. This negative pressure inside of container 95 draws fluid from a wound or opening in a body which is covered or at least adjacent to dressing 91. As fluid flows from a person's body through fluid conduit 93 it flows into container. A portion, or in at least one embodiment a substantial portion, or even all of the fluid can be blood. As shown in FIG. 13 or 14, a coagulant or coagulating agent can be provided which coagulates or helps to solidify the body fluid such as blood into a more solid form. This more solid form of blood is then trapped by at least one filter such as any one of filters 145 and/or filter 140 so that the blood/body fluid does not flow into the pump. If the blood/body fluid flows into the pump it could in some instances damage the components of the pump. Therefore, with this design, the filter-coagulant configuration, the coagulant-filter configuration or the filter-coagulant-filter configuration can be used to trap fluid inside the container to prevent damage to a pump.

Accordingly, while at least one embodiment of the present invention has been shown and described, it is obvious that many changes and modifications may be made thereunto without departing from the spirit and scope of the invention.

What is claimed is:

1. A process for removing body fluids from a body opening, comprising:
   providing a container for storing the body fluids;
   supporting the container via a stand such that the container extends in an oblique manner above a surface;
   pumping the body fluids from the body opening to the container using a pressure pump creating negative pressure in the container;
   providing at least one inflow port and at least one outflow port, the inflow port providing entry of the body fluids into the container;
   providing at least one filter fluidly coupled with the outflow port and disposed within a fluid conduit upstream of an outflow end of the outflow port;
   providing at least one coagulant, positioned upstream of the at least one filter within the conduit, for coagulation of the body fluids within the conduit;
   providing at least one additional filter within the conduit, the additional filter positioned upstream of the at least one coagulant and adjacent to the outflow end of the outflow port, the at least one additional filter for preventing body fluids from exiting the outflow port and damaging the pump;
   coagulating the body fluids with the at least one coagulant within the conduit between the at least one additional filter and the at least one filter to provide coagulated body fluids;
   storing the coagulated body fluids in the container; and
   removing at least one of said at least one filter and said at least one additional filter from the container.

2. The process as in claim 1, wherein said step of providing a container further comprises providing a container having at least one support arm for supporting said container over a surface, an inflow channel for receiving body fluids body fluid, and wherein said channel is an outflow channel, wherein said filter and said coagulant are disposed in said outflow channel.

3. The process as in claim 2, wherein said at least one support arm is positioned to bias said container to lean in a direction once said container is positioned on a surface.

4. The process as in claim 1, wherein said at least one filter comprises a PTFE filter.

5. The process as in claim 1, wherein said second at least one additional filter comprises a PTFE filter wherein said second at least one additional filter comprises a removable filter.

6. The process as in claim 1, further comprising the step of removing at least one frame configured to support said at least one filter.

7. The process as in claim 6, further comprising the step of grasping arms of said frame to remove said at least one frame.

8. A process for pumping fluid from an opening in a body, comprising:
   providing a container having an intake port and an outflow port;
   supporting the container via a stand such that the container extends in an oblique manner above a surface;
   coupling a first filter to said outflow port;
   positioning a coagulant adjacent to said first filter;
   inserting a second filter in said outflow port adjacent to said coagulant and opposite said first filter;
   fixing said second filter in said outflow port;
   coupling said intake port to a fluid conduit; and
   coupling said outflow port to a pump;
   removing at least one of said first filter and said second filter from said container; and
   pumping the fluid from the opening in the body into the container so that the fluid contacts said coagulant.

9. The process as in claim 8, wherein the steps of claim 8 are performed in order of their listing.

10. The process as in claim 8, further comprising the step of turning on said pump to draw fluid from a person's body.

11. The process as in claim 8, further comprising the step of coagulating body fluid inside of said container.

12. The process as in claim 11, further comprising the step of trapping said coagulated body fluid inside of said container, wherein said step of providing a container includes providing a container having at least one support arm to support said container above a surface, and wherein said at least one support arm is configured to bias said container in one direction.

13. The process as in claim 8, further comprising the step of removing at least one frame configured to support said at least one filter.

14. A container for receiving body fluid, comprising:
   a housing said housing comprising:
   i) a body having a base;
   ii) an intake port coupled to said body housing providing entry of the body fluids into the container;
   iii) an outflow port coupled to said body housing said outflow port having a conduit and an end;
   iv) a stand comprising supports coupled to the base said stand configured to support said housing in an oblique manner above a surface;
   at least one filter coupled to said housing disposed in said conduit of said outflow port adjacent to and upstream from said end;
   at least one coagulant, said coagulant being disposed in said conduit upstream of said at least one filter; and
   at least one additional filter disposed in said conduit and coupled to said coagulant opposite said at least one filter wherein said coagulant is disposed between said at least one filter and said at least one additional filter wherein said at least one filter and said at least one additional filter are removable.

15. The container as in claim 14, wherein said coagulant is a solidifier agent in powder form.

16. The container as in claim 14, wherein said at least one filter is a PTFE filter.

17. The container as in claim 14, wherein said at least one filter is a PTFE filter and the container further comprise
wherein said at least one additional filter comprises a PTFE filter that is removable, wherein said at least one additional filter comprises a solid backing structure;
wherein said coagulant is a solidifier agent which is in powder form and is disposed between said at least one filter and said at least one additional filter in said outflow port.

18. The process as in claim 14, further comprising the step of removing at least one frame configured to support said at least one filter.

19. The process as in claim 18, further comprising the step of grasping arms of said at least one frame to remove said at least one frame.

20. The container as in claim 14 wherein said stand comprises a plurality of supports which are positioned substantially offset from a center position on said base so as to support a lean of the device from one side to the other.

* * * * *